United States Patent
Khoshdel

(10) Patent No.: US 7,485,287 B2
(45) Date of Patent: Feb. 3, 2009

(54) METHOD OF STYLING HAIR WITH AQUEOUS BASED HAIR SPRAYS

(75) Inventor: Ezat Khoshdel, Wirral (GB)

(73) Assignee: Unilever Home & Personal Care USA Division of Conopco, Inc., Chicago, IL (US)

( * ) Notice: Subject to any disclaimer, the term of this patent is extended or adjusted under 35 U.S.C. 154(b) by 890 days.

(21) Appl. No.: 10/437,084

(22) Filed: May 13, 2003

(65) Prior Publication Data

US 2003/0206880 A1    Nov. 6, 2003

Related U.S. Application Data

(62) Division of application No. 10/037,066, filed on Nov. 7, 2001, now abandoned.

(30) Foreign Application Priority Data

Nov. 7, 2000    (GB) ................. 0027180.9

(51) Int. Cl.
*A61K 8/00* (2006.01)
*A61K 8/72* (2006.01)

(52) U.S. Cl. ................. 424/70.1; 424/70.11; 424/70.13

(58) Field of Classification Search .................. 424/70, 424/70.1, 70.11, 70.13
See application file for complete search history.

(56) References Cited

U.S. PATENT DOCUMENTS

| | | | |
|---|---|---|---|
| 5,631,244 A | 5/1997 | Galons et al. | |
| 5,854,225 A | 12/1998 | Richard et al. | |

FOREIGN PATENT DOCUMENTS

| | | | |
|---|---|---|---|
| EP | 0 246 090 | | 11/1987 |
| EP | 0246090 | * | 11/1987 |
| EP | 0 469 232 | | 2/1992 |
| EP | 0469232 A1 | | 2/1992 |
| EP | 0 579 435 | | 1/1994 |
| EP | 0579435 A1 | | 1/1994 |
| JP | 07309722 | * | 11/1995 |
| WO | 00/40211 | | 7/2000 |

OTHER PUBLICATIONS

Search Report under Section 17, Application No. GB 0027180.9 dated Apr. 23, 2001.
WPI Abstract Accession No. 96.045284/05 & JP 070309722 assigned to Shiseido.
International Search Report Application No. PCT/EP 01/12576 mailed Mar. 28, 2002.
D.C. Bibby: "Mechanisms by Which Cyclodextrins Modify Drug Release from Polymeric Drug Delivery Systems", International Journal of Pharmaceutics, vol. 197, 2000, pp. 1-11, XP00106623 NL.
Loftsson T: "Increasing the Cyclodextrin Complexation of Drugs and Drug Biovailability Through Addition of Wafer-Soluble Polymers", Pharmazie, Veb Verlag Volk Und Gesundheit, Berlin, DD, vol. 53, No. 11, (Nov. 1, 1998) pp. 733-740, XP000783396.
International Journal of Pharmeaceutics, *"Mechanism by which cyclodextrins modify drug rel4ease from polymeric drug delivery systems"*, D.C. Bibby, vol. 197, 2000, pp. 1-11.
Pharmazie 53, "Increasing the cyclodextrin complexation fo drugs and drug biovaliability through addition of water-soluble polymers", vol. 53, No. 11, pp. 733-740.
GB Search Report in a GB application GB 0027180.9.
Abstract of JP 070309722—published May 17, 1994.

* cited by examiner

*Primary Examiner*—Gina C Yu
(74) *Attorney, Agent, or Firm*—Karen E. Klumas

(57) ABSTRACT

Cosmetic or personal care compositions comprise from 0.01% to 10% by weight of a hair styling polymer comprising one or more hydrophobic groups, from 0.001% to 10% by weight of an optionally substituted cyclodextrin and a cosmetically acceptable diluent or carrier. The cyclodextrin complexes with the hydrophobic groups to increase the solubility of the hair styling polymer in the composition. The cyclodextrin thus allows the formulation of compositions with relatively higher water contents.

14 Claims, No Drawings

METHOD OF STYLING HAIR WITH AQUEOUS BASED HAIR SPRAYS

This is a divisional of U.S. application Ser. No. 10/037,066, filed Nov. 7, 2001, now abandoned.

FIELD OF THE INVENTION

This invention relates to cosmetic and personal care compositions, to a method of treating hair using the compositions and to the use of certain compounds to increase the solubility of a polymer in a cosmetic or personal care composition.

BACKGROUND AND PRIOR ART

The desire to have the hair retain a particular shape or style is widely held. The most common approach for accomplishing styling of hair is the application of a composition to dampened hair, after shampooing and/or conditioning, or to dry, styled hair. These compositions provide temporary styling benefits and can readily be removed by water or shampooing. To date, the materials employed in hair care compositions to provide styling benefits have generally been natural or synthetic resins and have been applied in the form of, for example, sprays, mousses, gels and lotions.

Recently, it has become desirable to have a high level of style retention, or strong hold, delivered from a hair spray composition. In a typical hair spray, hold is achieved by the use of commercially available styling polymers, such as AMPHOMER (™), supplied by National Starch Chemical Company, LUVIMER(™), supplied by BASF, GANTREZ (™), supplied by ISP Chemicals and also silicone graft copolymers, supplied by Mitsubishi Chemicals.

Typically, the styling polymers have a carbon backbone comprising various hydrophilic and hydrophobic vinylic monomers. These polymers can be nonionic or they can carry a charge, usually a negative charge. The hydrophilic monomer is employed to render the polymer water-soluble and the hydrophobic monomer is generally selected to enhance humidity resistance of the styling resins. Traditionally, the anionically charged resins are formed from the corresponding acids (neutralised) using alkalising agents such as sodium or potassium hydroxide as well as certain functional amines such as aminomethyl propanol (AMP) to tailor their solubility and film forming properties.

The hydrophobic/hydrophilic character of modern styling resins is carefully balanced to produce materials that are soluble in hydroalcoholic solvents, typically 80% volatile organics content (VOC). To improve the performance of modern styling products even further, non-volatile plasticisers such as propylene glycol, dipropylene glycol, acetyl tri-n-butyl citrate and acetyl tri-2-ethoxyhexyl citrate (Citroflex (™)) have been employed in the compositions.

The conventional hair styling compositions require a relatively high VOC in order to solubilise the hair styling polymer. It is desirable, for economic and environmental reasons, to reduce the VOC of hair styling compositions.

Cyclodextrins (CDs), are cyclic oligosaccharides which may be derived from starch, or which can be obtained in other ways. Cyclodextrins were discovered about 100 years ago and have been used in the pharmaceutical and food industries for encapsulation of drugs and flavours. Cyclodextrins have also been used as processing aids, to isolate compounds from natural sources and to remove unwanted compounds such as cholesterol from food products.

The natural CDs are produced from starch by the action of cyclodextrin glycosyl transferase (CGTase), an enzyme produced by several organisms. Structurally, CDs consist of 6, 7, 8 and 9 ($\alpha$, $\beta$, $\gamma$ and $\delta$, respectively) glucose units. They are typically shaped like conical tubes or buckets with a hydrophobic interior and a hydrophilic exterior. CDs are able to enclose a wide range of functional molecules as guests into their cavities, as described by, for example M L Bender; M Komiyama, Cyclodextrin Chemistry, Spring-Verlag, Berlin, 1978.

While there are many examples of inclusion complexes of small molecules with cyclodextrins in the literature, there are only few reports on the formation of such complexes with polymeric materials. For example, some attention has been given to produce polyrotaxanes containing cyclodextrins and side chain polyrotaxanes have been prepared and characterised (G. Wenz, Angew. Chem, Int. Ed. Eng. 1994, 33, 803 and M. Born and H. Ritter, Angew. Chem, Int. Ed. Eng. 1995, 34, 309).

Most recently, cyclodextrins have been utilised-in the free radical polymerisation field (J. Jeromin and H. Ritter, Macromol. Chem. Rapid Commun. 1998, 19, 377).

The use of cyclodextrins to remove odour in hair cosmetics is described in EP-A-0469232. Similarly, EP-A-0246090 teaches the use of cyclodextrins for the inhibition of perm odour.

A hair conditioning composition which comprises a visible breakable particle optionally comprising a cyclodextrin is disclosed in WO 00/40211. The compositions are not styling products and it is clear that any cyclodextrin could not assist in solubilising a polymer.

JP-A-7309722 describes hair cosmetic compositions comprising hydroxylated cyclodextrin and a high molecular weight silicone.

There is no suggestion in the prior art that a cyclodextrin could be used to increase the solubility of a polymer in a hair styling composition.

It is an aim of the present invention to provide cosmetic and personal care compositions in which the hair styling polymer has a greater aqueous solubility and which, therefore, may be formulated with a greater proportion of water as solvent.

It is a further aim of the present invention to provide other advantages in cosmetic and personal care compositions. For example, compositions of the invention may, surprisingly, have one or more advantageous properties selected from low tack polymer film characteristics, and when applied to hair can give improved hold of hair and/or enhanced shine of hair and/or better natural movement of hair.

SUMMARY OF THE INVENTION

According to the present invention, there is provided a cosmetic or personal care composition comprising from 0.01% to 10% by weight of a hair styling polymer comprising one or more hydrophobic groups, from 0.001% to 10% by weight of an optionally substituted cyclodextrin and a cosmetically acceptable diluent or carrier, wherein the optionally substituted cyclodextrin complexes with the hydrophobic groups to increase the solubility of the hair styling polymer in the composition.

In another aspect, the invention provides the use of an optionally substituted cyclodextrin to increase the solubility of a hair styling polymer in a cosmetic or personal care composition. The solubility of the hair styling polymer is increased in the composition relative to a cosmetic or personal care composition containing the same components but without the cyclodextrin.

In yet another aspect, the invention provides a cosmetic method of treating hair which comprises applying to the hair a composition of the invention.

DETAILED DESCRIPTION OF THE INVENTION

The present invention relates to cosmetic and personal care compositions (for example, hair styling compositions) comprising a cyclodextrin.

Surprisingly, it has been found that hair styling polymers can be solubilised in aqueous or aqueous rich hydroalcoholic solutions, and other aqueous solvent systems, by employing a variety of cyclodextrins or derivatives thereof. Without wishing to be bound by theory, it is believed that the cyclodextrin complexes with the hydrophobic moieties present in the styling resin and masks the hydrophobic character of the polymer. Therefore, the complexation leads to the solubilisation of hair styling polymers in aqueous or aqueous rich hydroalcoholic formulations. The cyclodextrin-complexed hair styling polymers can also be neutralised with conventional neutralisers and can also be modified with conventional plasticisers.

The term complexation and related terms used herein are well-known to those skilled in the art and refer to any interaction and/or association at a molecular level between the cyclodextrin and the hair styling polymer, which does not involve the formation of covalent bonds.

Cyclodextrins

The compositions of the invention may comprise a single cyclodextrin or a mixture of different cyclodextrins.

The cyclodextrins used in the invention can be obtained wholly or partly from natural starch or can be wholly or partly synthetic.

Cyclodextrins which may be used in the invention include α-, β-, γ- and δ-cyclodextrins, optionally substituted. The cyclodextrins may be used in the composition in the form of a hydrate, and/or a salt when the optional substituent comprises one or more acidic or basic groups.

A range of optionally substituted cyclodextrins is commercially available.

Optional substituents on the cyclodextrin include groups attached to oxygen and/or carbon atoms of the cyclodextrin. Suitable substituents, include, for example: anionic groups (such as sulphate, phosphate or carboxylate); mono-, di-, tri- or polyethers obtainable by alkylation of one or more oxygen atoms with one or more $C_1$ to $C_6$ alkyl groups (such as 2-hydroxyethyl or 2-hydroxypropyl); carboxyalkyl groups, wherein the alkyl group is $C_1$ to $C_6$ alkyl (such as 2-carboxyethyl); and compounds formed by condensation of the cyclodextrins with a mono-or di-saccharide (eg, D-glucose to form an α-D-glucosyl derivative or maltose to form an α-maltosyl derivative).

The term "alkyl", as used herein, includes straight chain and, for alkyl groups containing three or more carbon atoms, branched groups. Examples of straight chain alkyl include methyl, ethyl, propyl, butyl, pentyl and hexyl. Examples of branched alkyl include isopropyl, isobutyl and tert-butyl.

Commercially available CDs which may be used in the invention include, for example: α-cyclodextrin; β-cyclodextrin hydrate; β-cyclodextrin sulphate, sodium salt; α-cyclodextrin hydrate; γ-cyclodextrin hydrate; (2-carboxyethyl)-β-cyclodextrin; (2-hydroxyethyl)-β-cyclodextrin; (2-hydroxypropyl)-α-cyclodextrin; (2-hydroxypropyl)-β-cyclodextrin; (2-hydroxypropyl))-γ-cyclodextrin; 2,6-di-O-methyl-β-cyclodextrin; heptakis(2,6-di-O-methyl)-β-cyclodextrin; 6-O-α-D-glucosyl-β-cyclodextrin; 6-O-α-maltosyl-β-cyclodextrin hydrate.

The optionally substituted cyclodextrin is present in the compositions of the invention in an amount of from 0.001% to 10% by weight (based on the total weight of the composition), more preferably 0.01% to 1% by weight most preferably 0.1% to 1% by weight (eg, 0.1% to 0.8% by weight). If the cyclodextrin is used in the form of a hydrate, the amounts by weight exclude any water of hydration.

For a given styling resin, the skilled person can determine the most suitable cyclodextrin to select for the compositions of the invention, based on standard techniques. For example, the complexation process can be investigated by visual observation of the polymer solution turbidity as well as Nuclear Magnetic Resonance (NMR) studies. Usually, the complexation affects the chemical shifts of the complexed species. The complexation process can be further investigated by microscopy and centrifugation, for example.

Hair Styling Polymer

The compositions of the invention comprise from 0.01% to 10% by weight (of the total composition), preferably 0.1% to 10% by weight, of a hair styling polymer. The amount of the polymer may, for example, range from 0.5% to 10%, preferably 0.75% to 6% by weight based on total weight of the composition.

Hair styling polymers are used, for example, in hair styling compositions such as hair sprays, gels, and mousses. Hair styling polymers are well known articles of commerce and many such polymers are available commercially which contain moieties which render the polymers cationic, anionic, amphoteric or nonionic in nature. Suitable hair styling polymers include, for example, block and graft copolymers. The polymers may be synthetic or naturally derived.

Examples of Anionic Hair Styling Polymers are
copolymers of vinyl acetate and crotonic acid;
terpolymers of vinyl acetate, crotonic acid and a vinyl ester of an alpha-branched saturated aliphatic monocarboxylic acid such as vinyl neodecanoate;
copolymers of methyl vinyl ether and maleic anhydride (molar ratio about 1:1) wherein such copolymers are 50% esterified with a saturated alcohol containing from 1 to 4 carbon atoms such as ethanol or butanol;
acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Preferably, the compositions of the invention comprise from 0.01% to 10% (preferably from 0.01% to 5%) by weight silicone, based on the total weight of the composition.

Specific Examples of Suitable Anionic Hair Styling Polymers are
RESYN® 28-2930 available from National Starch (vinyl acetate/crotonic acid/vinyl neodecanoate copolymer);
ULTRAHOLD® 8 available from BASF (CTFA designation Acrylates/acrylamide copolymer);

the GANTREZ®ES series available from ISP Corporation esterified copolymers of methyl vinyl-ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homodolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are crosslinked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific Examples of Suitable Cationic Polymers are
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as optional components in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macrografted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

Preferred hair styling polymers for use in the compositions of the invention comprise one or more of the same or different hydrophobic groups. Hydrophobic groups are those groups which confer hydrophobic character on the polymer, preferably relative to polar and/or charged groups also present in the polymer. The hydrophobic groups are preferably selected from: $C_1$-$C_{24}$ alkyl, $C_2$-$C_{24}$ alkenyl or $C_2$-$C_{24}$ alkynyl; $C_1$-$C_{24}$ alkyl, $C_2$-$C_{24}$ alkenyl or $C_2$-$C_{24}$ alkynyl, each of the latter three groups being optionally substituted with aryl, and mixtures thereof. More preferably, the hydrophobic groups are selected from: $C_4$-$C_{24}$ alkyl, $C_4$-$C_{24}$ alkenyl or $C_4$-$C_{24}$ alkynyl; $C_4$-$C_{24}$ alkyl, $C_4$-$C_{24}$ alkenyl or $C_4$-$C_{24}$ alkynyl, each of the latter three groups being optionally substituted with aryl, and mixtures thereof. Even more preferably, the hydrophobic groups are selected from: $C_6$-$C_{24}$ alkyl, $C_6$-$C_{24}$ alkenyl or $C_6$-$C_{24}$ alkynyl; $C_6$-$C_{24}$ alkyl, $C_6$-$C_{24}$ alkenyl or $C_6$-$C_{24}$ alkynyl, each of the latter three groups being optionally substituted with aryl, and mixtures thereof. For example, the hydrophobic groups may be selected from: $C_8$-$C_{18}$ alkyl, $C_8$-$C_{18}$ alkenyl or $C_8$-$C_{18}$ alkynyl; $C_8$-$C_{18}$ alkyl, $C_8$-$C_{18}$ alkenyl or $C_8$-$C_{18}$ alkynyl, each of the latter three groups being optionally substituted with aryl, and mixtures thereof.

The terms "alkenyl" and "alkynyl" are defined similarly to the term "alkyl" but the groups contain one or more carbon-carbon double or triple bonds, respectively.

The term "aryl" includes phenyl, optionally substituted (e.g., with from one to five alkyl groups).

Particularly preferred polymers for use in the compositions of the invention comprise carboxylic acid groups and/or salts thereof and/or esters thereof with $C_1$-$C_{12}$ (more preferably $C_4$-$C_{12}$, even more preferably $C_6$-$C_{12}$, such as $C_8$-$C_{12}$) alcohols and/or amides thereof with $C_1$-$C_{12}$ (more preferably $C_4$-$C_{12}$, even more preferably $C_6$-$C_{12}$, such as $C_6$-$C_{12}$) amines. The alcohols and amines preferably comprise straight chain alkyl groups.

Neutralising Agents

With certain of the above-described hair styling polymers, it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001% to about 10% by weight of the total composition.

Compositions of the Invention

Compositions of the present invention are preferably formulated into hair care compositions, especially hairspray compositions, but can also be formulated into a wide variety of product types, including mousses, gels, lotions, tonics, sprays, shampoos, conditioners, rinses, hand and body lotions, facial moisturisers, sunscreens, anti-acne preparations, topical analgesics, mascaras, and the like. Compositions of the invention comprise a cosmetically acceptable diluent or carrier. Preferably, the compositions are for use in styling human hair and, more preferably, they are packaged and labelled as such.

A particularly preferred composition according to the invention is a hair spray composition comprising:
 (i) from 0.01% to 10% (preferably from 0.1% to 10%) by weight of a hair styling polymer;
 (ii) from 0.001% to 10% (preferably from 0.01% to 1%) by weight of an optionally substituted cyclodextrin;
 (iii) optionally, from 0.001% to 10% (preferably from 0.01% to 5%) by weight of a neutraliser;
 (iv) optionally, from 0.01% to 5% by weight of a silicone;
 (v) at least 20% (preferably at least 50%) by weight water; and
 (vi) up to 50% by weight of a propellant.

The carriers and additional components required to formulate cosmetic and personal care compositions of the invention vary with product type and can be routinely chosen by one skilled in the art. The following is a description of some of these carriers and additional components.

Carriers

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, by weight of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular composition to be used, and on whether the product formulated is meant to be left on the surface to which it is applied (e.g., hair spray, mousse, tonic, or gel) or rinsed off after use (e.g., shampoo, conditioner, rinse).

The carriers used herein can include a wide range of components conventionally used in hair care compositions. The carriers can contain a solvent to dissolve or disperse the particular composition being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Suitable spray containers are well known in the art and include conventional, non-aerosol pump sprays i.e., "atomisers", aerosol containers or cans having propellant, as described above, and also pump aerosol containers utilising compressed air as the propellant.

Where the hair care compositions are conditioners and rinses, the carrier can include a wide variety of conditioning materials. Where the hair care compositions are shampoos, the carrier can include, for example, surfactants, suspending agents, and thickeners. Hair styling creams or gels also typically contain a structurant or thickener, typically in an amount of from 0.01% to 10% by weight.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurised aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents. (e.g., where the viscosity of the solvent has been increased to form a solid or semi-solid by the addition of appropriate gums, resins, waxes, polymers, salts, and the like).

The compositions of the present invention preferably comprise, amongst other carriers, water and ethanol, with the amount of water being preferably at least 20% by weight of the composition, more preferably at least 40% by weight (such as at least 50% by weight), more preferably at least 60% by weight, more preferably at least 70% by weight, even more preferably at least 80% by weight of the composition. The ratio of water to organic solvent (including, for example, ethanol) may preferably vary from 1:4 to 10:1, more preferably 1:1 to 10:1, most preferably 2:1 to 10:1. The compositions may, alternatively, contain water as the only solvent ie, have a VOC of 0%.

Additional Components

A wide variety of additional components can be employed in cosmetic and personal care compositions according to the present invention. Examples include the following:

- a perfume or fragrance, for example in an amount of from 0.01% to 1% by weight of the total composition.
- sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.
- anti-dandruff actives such as zinc pyrithione, piroctone olamine, selenium disulphide, sulphur, coal tar, and the like.
- hair conditioning agents such as hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.
- surfactants for hair shampoo and conditioner compositions. For a shampoo, the level is preferably from about 10% to about 30%, preferably from 12% to about 25%, by weight based on total weight of the composition. For conditioners, the preferred level of surfactant is from about 0.2% to about 3%, by weight based on total weight of the composition. Surfactants useful in compositions of the present invention include anionic, nonionic, cationic, zwitterionic and amphoteric surfactants.
- carboxylic acid polymer thickeners for hair shampoo and conditioner compositions. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and derived from a polyhydric alcohol. Examples of carboxylic acid polymer thickeners useful herein are those selected from the group consisting of carbomers, acrylates/C10-C30 alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners, by weight based on total weight of the composition.
- emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.
- vitamins and derivatives thereof (e.g., ascorbic acid, vitamin E, tocopheryl acetate, retinoic acid, retinol, retinoids, and the like).
- cationic polymers (e.g., cationic guar gum derivatives such as guar hydroxypropyltrimonium chloride and hydroxypropyl guar hydroxypropyltrimonium chloride, available as the Jaguar® series from Rhone-Poulenc).
- preservatives, antioxidants, chelators and sequestrants; and aesthetic components such as fragrances, colourings, hair nutrients and essential oils.

The following non-limiting Examples further illustrate the preferred embodiments of the invention. All percentages referred to are by weight based on total weight unless otherwise indicated.

EXAMPLES

Example 1

Improved Solubility of Hair Styling Polymers in Aqueous Compositions Containing a Cyclodextrin For the solubility tests summarised in Table 1, Amphomer® was used as the hair styling polymer Amphomer® is an octylacrylamide/acrylates/butylaminoethyl methacrylate copolymer sold by the National Starch and Chemical Corporation.

Tests 1, 3, 4 and 5 were carried out according to Protocol 1. Test 2 was carried out according to Protocol 2.

Protocol 1:
1. A beaker was charged with a known amount of water
2. A known amount of CD was added while stirring to form a solution
3. A known amount of Amphomer® was added and stirred magnetically
4. A visual observation was made to determine Amphomer® solubility Protocol 2:
1. A beaker was charged with 9.5 g ethanol and 9.9 g of water
2. 0.1 g CD powder was mixed with 0.5 g Amphomer® powder in another beaker
3. The contents of step 2 were poured into beaker 1 and the mixture stirred
4. A visual observation was made to determine Amphomer® solubility

TABLE 1

Improved Solubility of an Amphomer ® in Aqueous Ethanol [50:50 $H_2O$/EtOH w/w] solution in the presence of a cyclodextrin.

| Test | Amphomer (g) | CD Type (g) | Water (g) | Ethanol (g) | % VOC | Observation |
|---|---|---|---|---|---|---|
| 1 | 0.5 | 0 | 10 | 9.5 | — | Insoluble white lumps Suspension |
| 2 | 0.5 | α-CD (0.1) | 9.9 | 9.5 | — | Soluble-milky solution |
| 3 | 0.5 | β-CD | 9.9 | 9.5 | 47.5 | Soluble- |

TABLE 1-continued

Improved Solubility of an Amphomer® in Aqueous Ethanol [50:50 H₂O/EtOH w/w] solution in the presence of a cyclodextrin.

| Test | Amphomer (g) | CD Type (g) | Water (g) | Ethanol (g) | % VOC | Observation |
|---|---|---|---|---|---|---|
|  |  | (0.1) |  |  |  | white milky solution |
| 4 | 0.5 | γ-CD (0.1) | 9.9 | 9.5 | 47.5 | Soluble-white milky solution |
| 5 | 0.6 | SSβ-CD* (0.1) | 9.9 | 9.5 | — | Soluble-milky solution |

*β-cyclodextrin sulphate, sodium salt

The results given in Table 1 show that a variety of cyclodextrins can solubilise Amphomer®.

Similar Amphomer® compositions comprising the plasticisers silicone or dipropylene glycol or the neutralisers AMP or KOH were shown to form soluble clear or milky solutions.

Example 2

Tests were carried out according to Protocol 1 to determine that a range of different hair styling polymers are soluble in compositions containing a cyclodextrin. The results are shown in Table 2.

TABLE 2

Solubility data of several styling resins-CD complexes

| Styling Resin (g) | CD Type (g) | Water (g) | Ethanol (g) | % VOC | Observation |
|---|---|---|---|---|---|
| Amphomer® (0.5) | β-CD (0.1) | 9.9 | 9.5 | 47.5 | Soluble-white milky solution |
| Luviskol® (0.5) | α-CD (0.1) | 9.9 | 8.75 | 45.45 | Soluble-clear solution |
| Luviskol® (0.4) | β-CD (0.1) | 8.9 | 0.6 | 6 | Soluble-clear solution |
| Luviskol® (0.4) | α-CD (0.1) | 8.9 | 0.6 | 6 | Soluble-clear solution |
| SCJ® (2.4) | α-CD (0.1) | 7.5 | 0 | 0 | Soluble-clear solution |
| Amphomer® (0.5) | γ-CD (0.1) | 9.9 | 9.5 | 47.5 | Soluble-white milky solution |

Data presented in table 2 show that Amphomer®, Luviskol® and SCJ® could be solubilised by employing α-, β- and γ-CD.

Luviskol® is Luviskol VA 37 HM, a copolymer of vinylpyrrolidone and vinyl acetate available from BASF. SCJ is a copolymer of methacrylic acid, ethyl methacrylate and butyl acrylate, available from S C Johnson.

Examples 3 to 5

The following are examples of compositions according to the invention.

TABLE 3 examples of compositions of the invention

| Example | Ingredient | % by weight |
|---|---|---|
| 3 | Amphomer | 2.75 |
|  | AMP | 0.4 |
|  | α-CD | 0.25 |
|  | Ethanol | 47.3 |
|  | Water | 49.3 |
| 4 | Amphomer | 3 |
|  | AMP | 0.25 |
|  | α-CD | 0.25 |
|  | DPG* | 0.05 |
|  | Ethanol | 46.8 |
|  | Water | 49.65 |
| 5 | Amphomer | 3 |
|  | AMP | 0.25 |
|  | α-CD | 0.25 |
|  | Silicone | 0.05 |
|  | Ethanol | 46.8 |
|  | Water | 49.65 |

Dipropyleneglycol

Examples 3 to 5 may be formulated together with up to 1% of conventional minor additives such as, for example, preservatives and fragrance/perfume, with the amount of minors being deducted from the amount of water present in the composition.

In comparative tests against a control composition containing (in weight percent): Amphomer (2.5%); AiMP (0.5%); ethanol (55%); and water (42%), the compositions of Examples 3 to 5 were found to give superior hold in mannequin head tests, as determined by twelve panellists.

The invention claimed is:

1. A cosmetic method of styling hair to achieve increased style retention and hold, the method comprising the step of spraying onto the hair an aqueous or aqueous/solvent based hair spray composition comprising:
   i) from 0.01% to 10% by weight of a hair styling polymer comprising one or more carboxylic acid derived monomers selected from the group consisting of a carboxylic acid, a carboxylic acid salt, an ester of a C1 to C12 alcohol, an amide on a C1 to C12 amine, and mixtures thereof; and one or more hydrophobic monomers containing a C4 to C24 alkyl group;
   ii) from 0.001% to 10% by weight of an optionally substituted cyclodextrin;
   iii) a cosmetically acceptable carrier comprising water or a mixture of water and a solvent, and
   iv) an alkaline neutralizing agent for the styling polymer, wherein the optionally substituted cyclodextrin increases the solubility of the hair styling polymer in the aqueous or aqueous/solvent based, hair spray composition, and wherein the hair spray composition comprises at least 50% water by weight.

2. The method according to claim 1 wherein the optionally substituted cyclodextrin is present in an amount from 0.01 to 1% by weight.

3. The method according to claim 1 wherein the cyclodextrin is an α-, β-, or γ-cyclodextrin, optionally substituted.

4. The method according to claim 1 wherein the cyclodextrin is α-cyclodextrin.

5. The method according to claim 1 wherein the cyclodextrin is β-cyclodextrin sulfate or a salt thereof.

6. The method according to claim 1 wherein the hair styling polymer is present in an amount of from 0.1% to 10% by weight.

7. The method according to claim 1 wherein the hair styling polymer is selected from the group consisting of copolymers of $C_4$ to $C_{12}$ acrylamide, acrylates or methacrylates, and butylaminoethyl methacrylates, and copolymers of methacrylic acid, ethyl methacrylate, and $C_4$ to $C_{12}$ acrylates, and mixtures thereof.

8. The method according to claim 1 wherein the hydrophobic monomer of the hair styling polymer contains a $C_6$ to a $C_{12}$ alkyl group.

9. The method according to claim 1 wherein the solvent is ethanol.

10. The method according to claim 1 wherein the hair spray composition further comprises up to 50% propellant by weight.

11. The method according to claim 1 wherein the hair spray composition is applied from a pump spray.

12. A method of increasing the solubility of hair styling polymers containing monomers having hydrophobic pendant groups in an aqueous or aqueous/solvent based hair spray composition, the method comprising the step of
   i) adding to the composition an optionally substituted cyclodextrin in an amount from between 0.001% to 10% by weight of the hair spray composition, wherein the hair styling polymer comprises one or more carboxylic acid derived monomers selected from the group consisting of a carboxylic acid, a carboxylic acid salt, an ester of a C1 to C12 alcohol, an amide on a C1 to C12 amine and mixtures thereof; and one or more hydrophobic monomers containing a C4 to C24 alkyl group and wherein the hydrophobic polymer is less soluble in the composition in the absence of the optionally modified cyclodextrin.

13. The method according to claim 1 wherein the hair spray composition comprises at least 70% water by weight.

14. The method according to claim 1 wherein the hair spray composition has a ratio of water to organic solvent of from 1:1 to 10:1.

* * * * *